US00PP37596P2

(12) United States Plant Patent
Mislow, III

(10) Patent No.: US PP37,596 P2
(45) Date of Patent: Aug. 18, 2026

(54) ***FICUS* PLANT NAMED 'GM3X25002'**

(50) Latin Name: *Ficus Lyrata*
Varietal Denomination: GM3X25002

(71) Applicant: Gregory J. Mislow, III, Miami, FL (US)

(72) Inventor: Gregory J. Mislow, III, Miami, FL (US)

( * ) Notice: Subject to any disclaimer, the term of this patent is extended or adjusted under 35 U.S.C. 154(b) by 0 days.

(21) Appl. No.: 19/204,041

(22) Filed: May 9, 2025

(51) Int. Cl.
*A01H 5/00* (2018.01)
*A01H 6/00* (2018.01)

(52) U.S. Cl.
USPC ..... Plt./211

(58) Field of Classification Search
USPC ..... Plt./211
See application file for complete search history.

(56) References Cited

U.S. PATENT DOCUMENTS

PP9,323 P * 10/1995 van der Knaap ..... Plt./211

* cited by examiner

*Primary Examiner* — Susan McCormick Ewoldt
*Assistant Examiner* — Zachariah Allan Kay
(74) *Attorney, Agent, or Firm* — The Webb Law Firm

(57) ABSTRACT

A new and distinct variety of *Ficus* plant having serrated dark green leaves that grows more compactly in partial shade.

13 Drawing Sheets

Botanical classification: *Ficus Lyrata.*
Varietal denomination: 'GM3X25002'.

BACKGROUND OF THE NEW PLANT

The present invention relates to a new and distinct cultivar of *Ficus*, botanically known as *Ficus Lyrata.*

The new *Ficus* was discovered by the Inventor in October 2024, in a controlled environment in a nursery in Miami, Florida. The parent plants are unknown. Asexual propagation of the new cultivar by cuttings since February 2025, in Miami, Florida, has shown that the unique features of this new *Ficus* are stable and reproduced true to type in successive generations.

SUMMARY OF THE INVENTION

The following traits have been repeatedly observed and are determined to be unique characteristics of the new *Ficus*. These characteristics in combination distinguish the new *Ficus* as a new and distinct cultivar:

1. Narrow leaf
2. Serrated edged leaf
3. Compact
4. Small leaf
5. Dark green

Plants of the new *Ficus* can be compared to the plants of the *Ficus* cultivar 'Bambino', patented as U.S. Plant Pat. No. 9,323P. In side-by-side comparisons conducted by the Inventor in Miami, Florida, plants of the new *Ficus* differed from plants of the cultivar 'Bambino' in the following characteristics:

1. The claimed plant has a serrated leaf
2. The claimed plant has a narrow leaf
3. The claimed plant has a longer leaf

BRIEF DESCRIPTION OF THE DRAWINGS

The accompanying colored photographs illustrate the overall appearance of the new *Ficus*, showing the colors as true as it is reasonably possible to obtain in colored reproductions of this type. Colors in the photographs may differ slightly from the color values cited in the detailed botanical description, which accurately describes the colors of the new *Ficus.*

The photograph of FIG. 1 comprises a side perspective view of a typical plant of the new *Ficus.*

Figure 1:
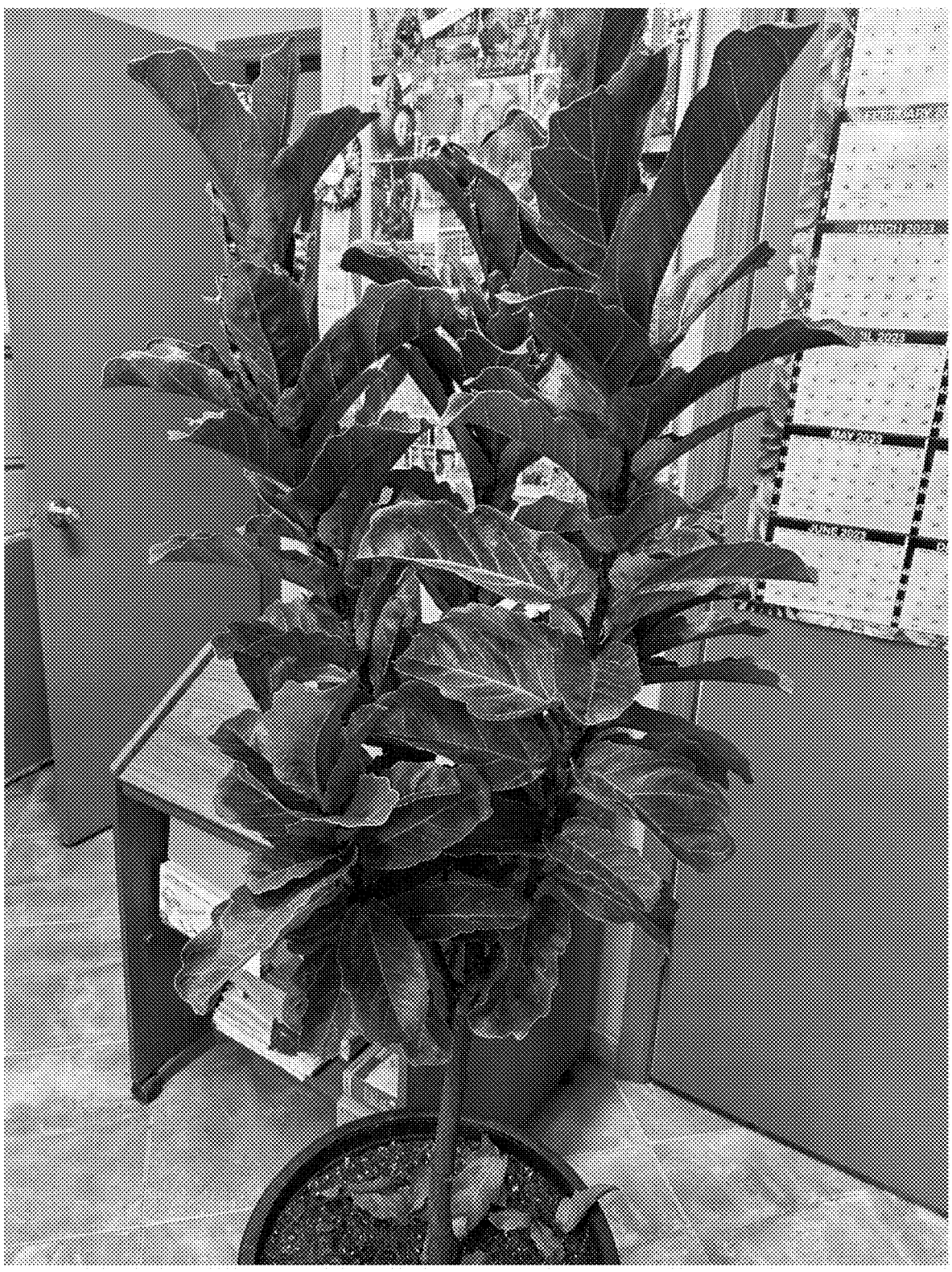
Figure 2:
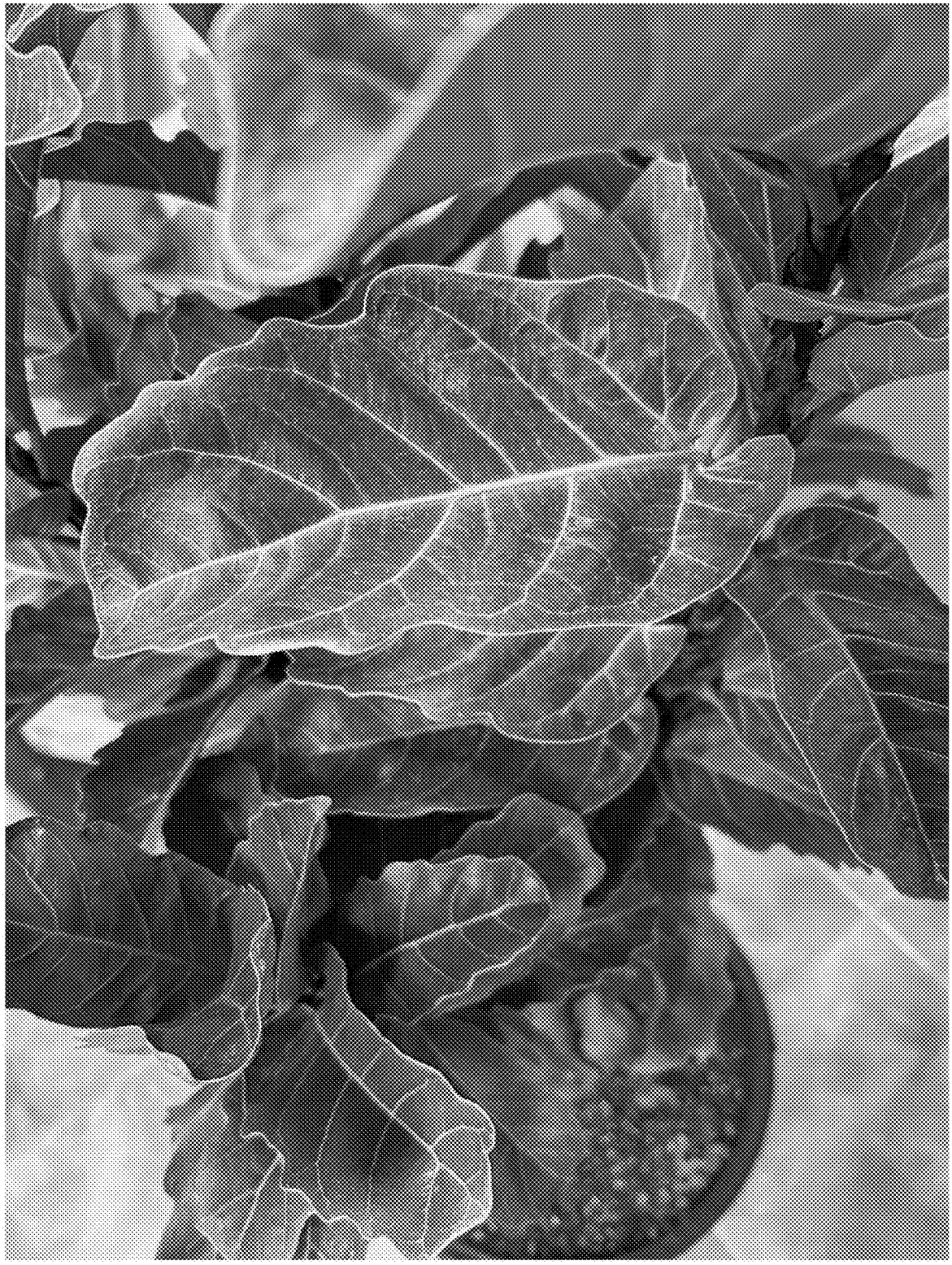

The photograph of FIG. 2 comprises a close-up view of typical leaves of the new *Ficus.*

Figure 3:
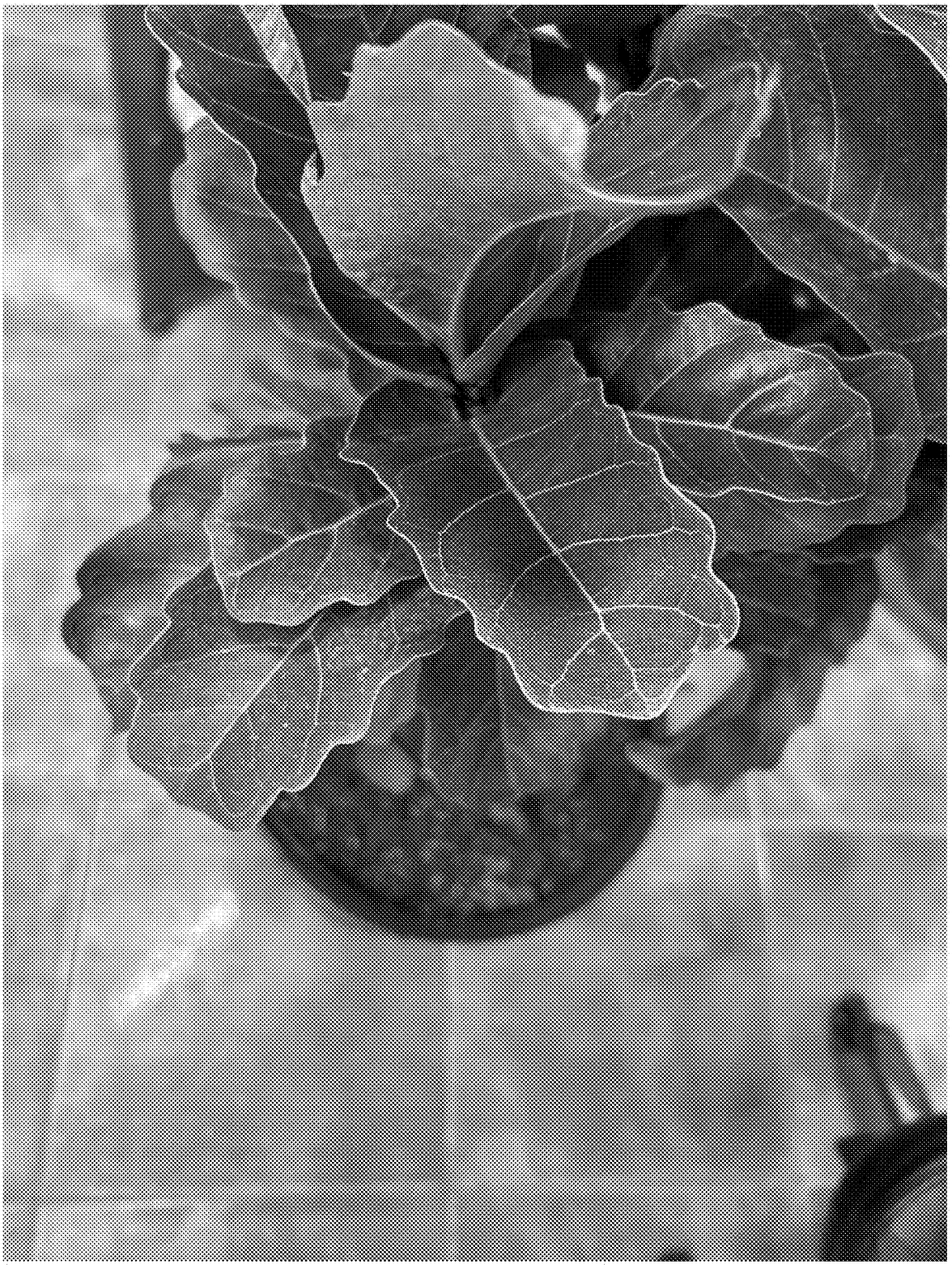

The photograph of FIG. 3 comprises a close-up view of typical leaves of the new *Ficus.*

Figure 4:
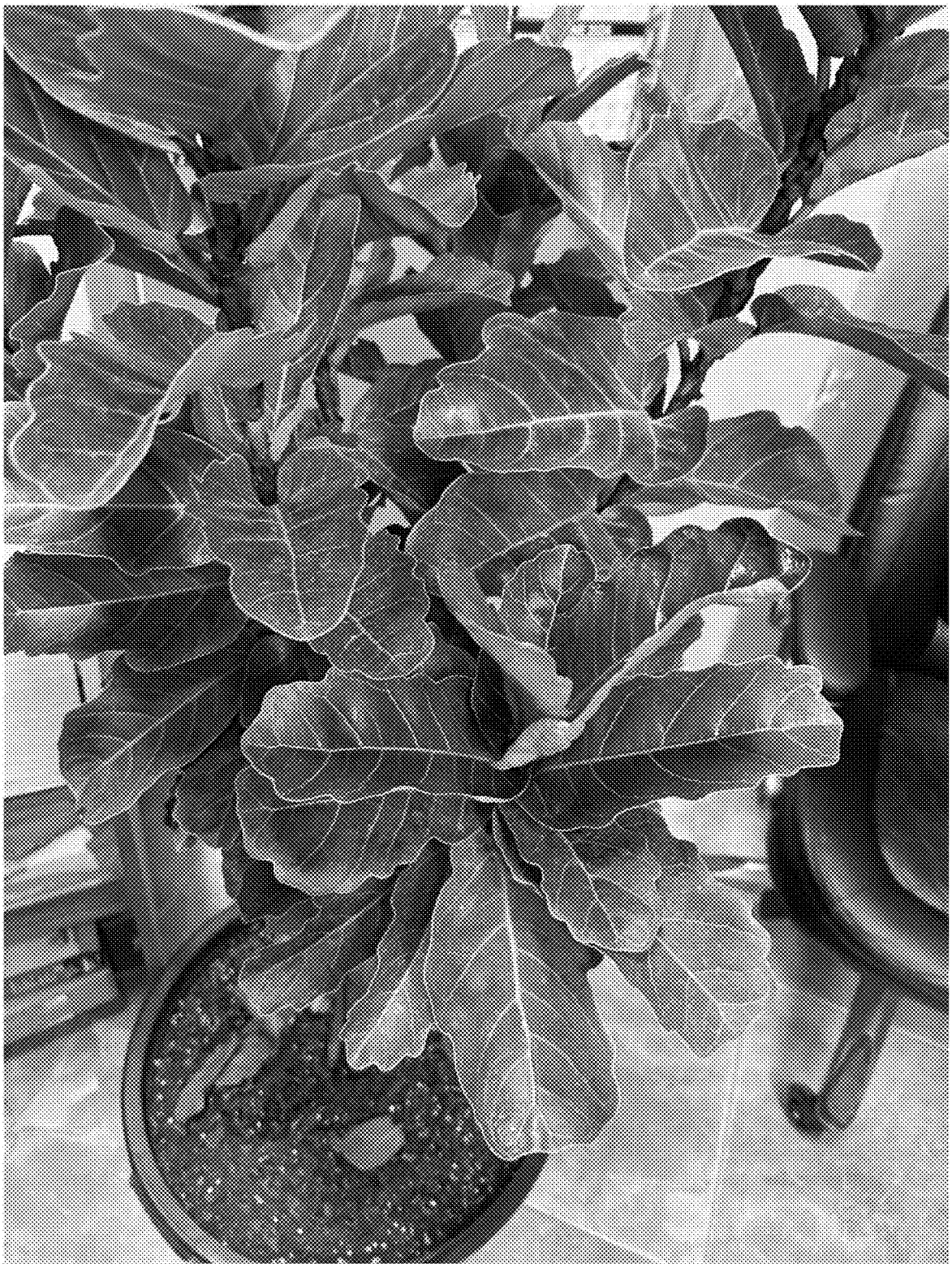

The photograph of FIG. 4 comprises a side perspective view of a typical plant of the new *Ficus.*

Figure 5:
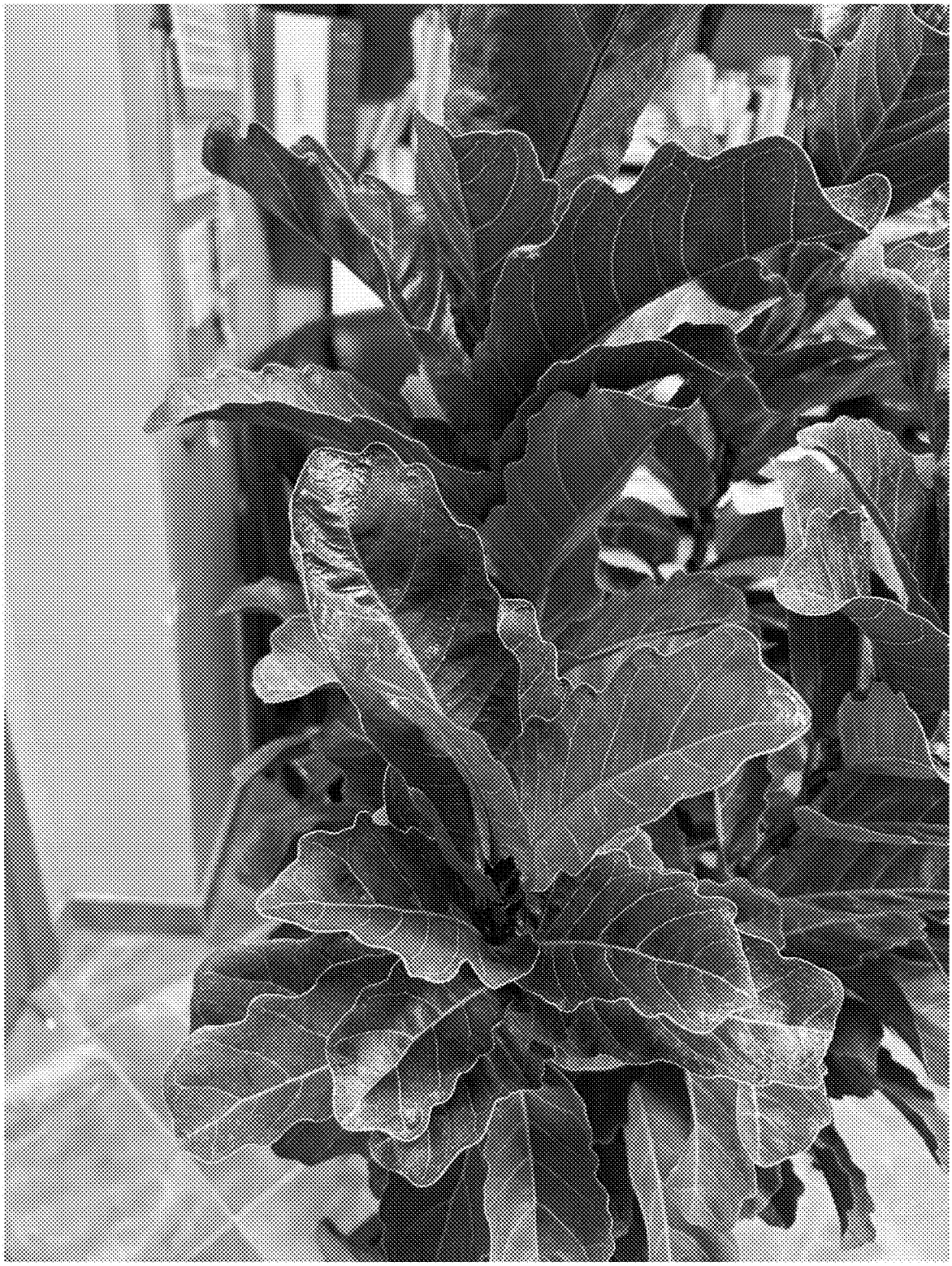

The photograph of FIG. 5 comprises a side perspective view of a typical plant of the new *Ficus.*

Figure 6:
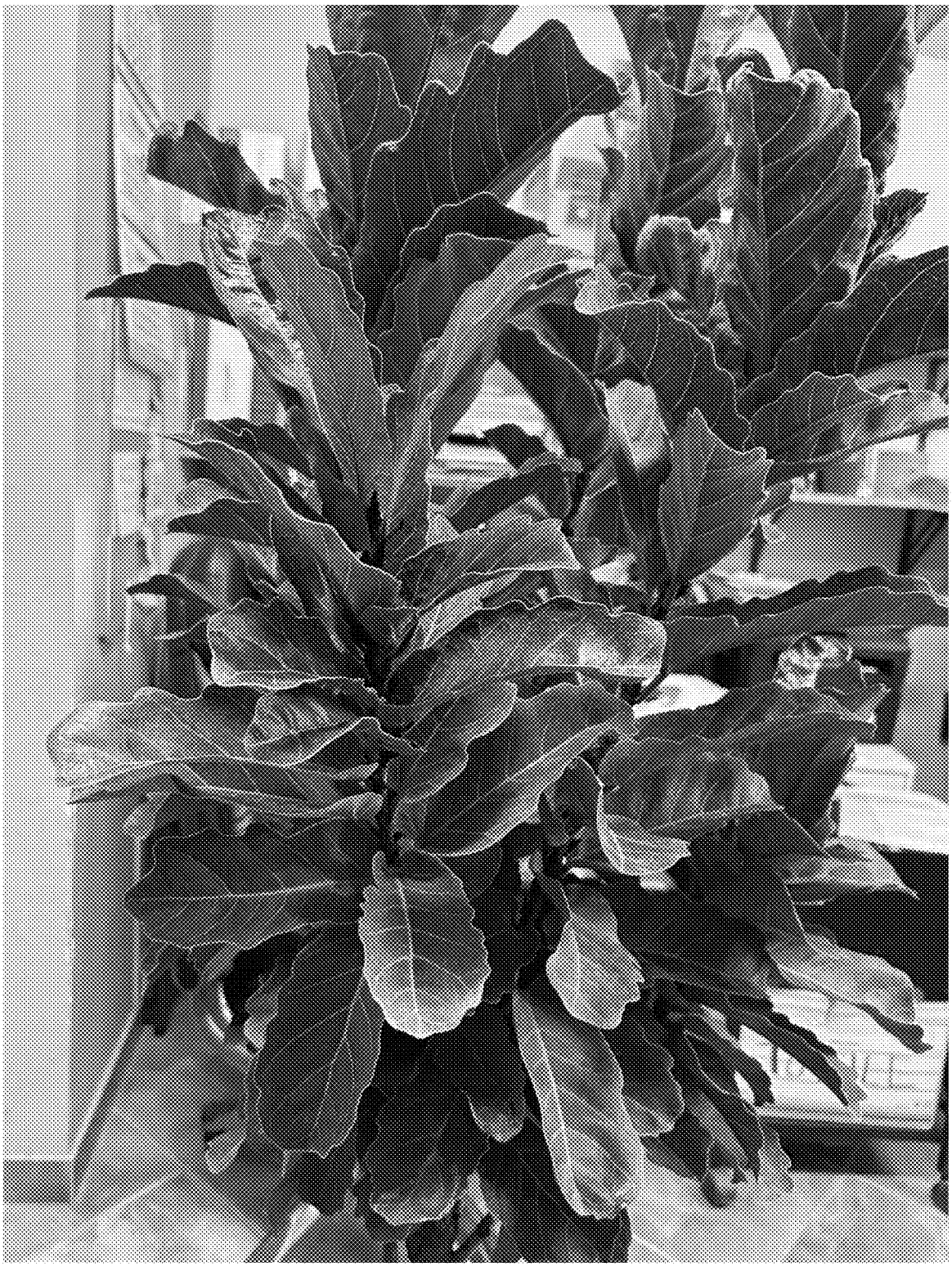

The photograph of FIG. 6 comprises a side perspective view of a typical plant of the new *Ficus.*

Figure 7:
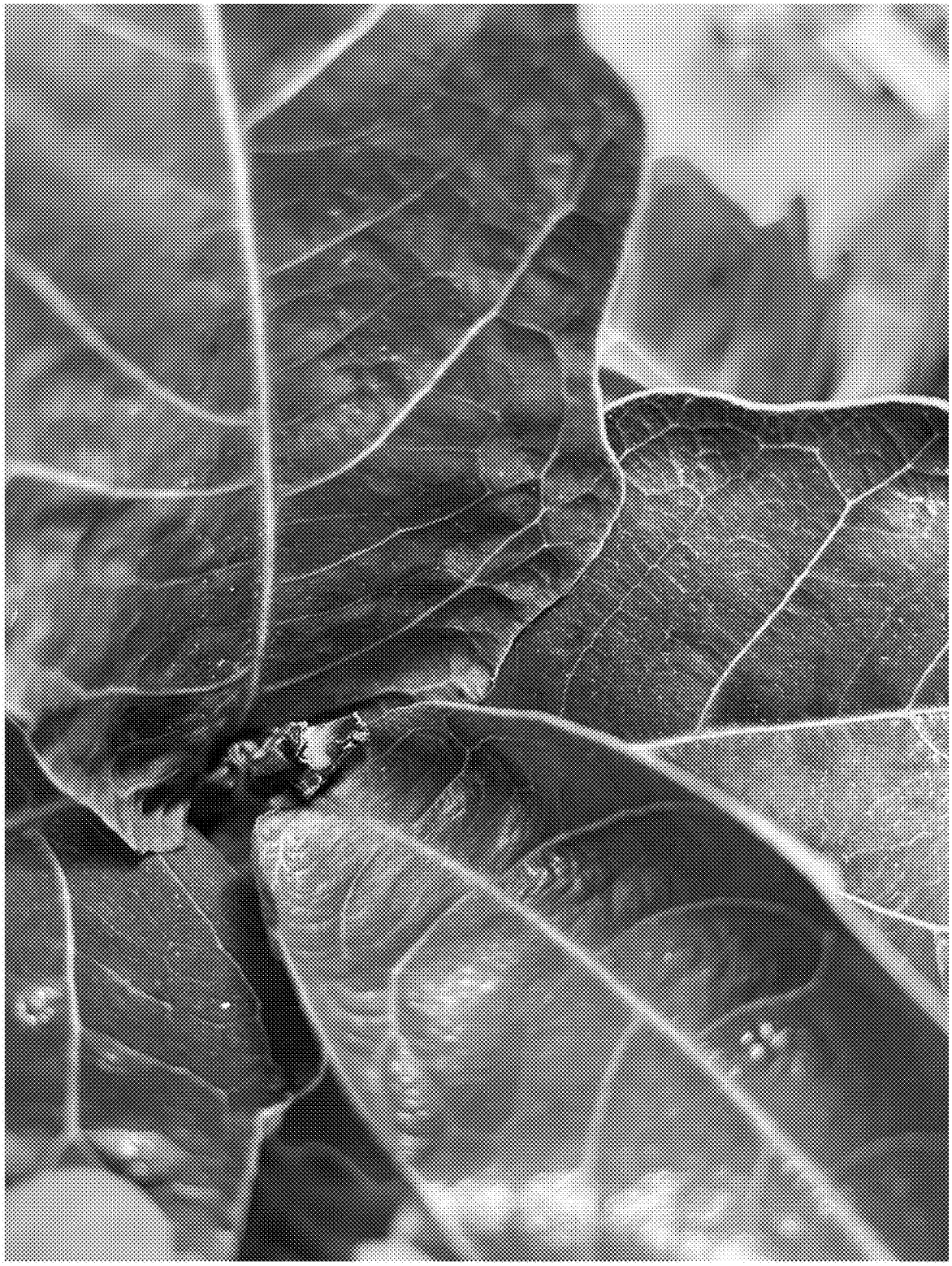

The photograph of FIG. 7 comprises a close-up view of typical leaves of the new *Ficus.*

Figure 8:
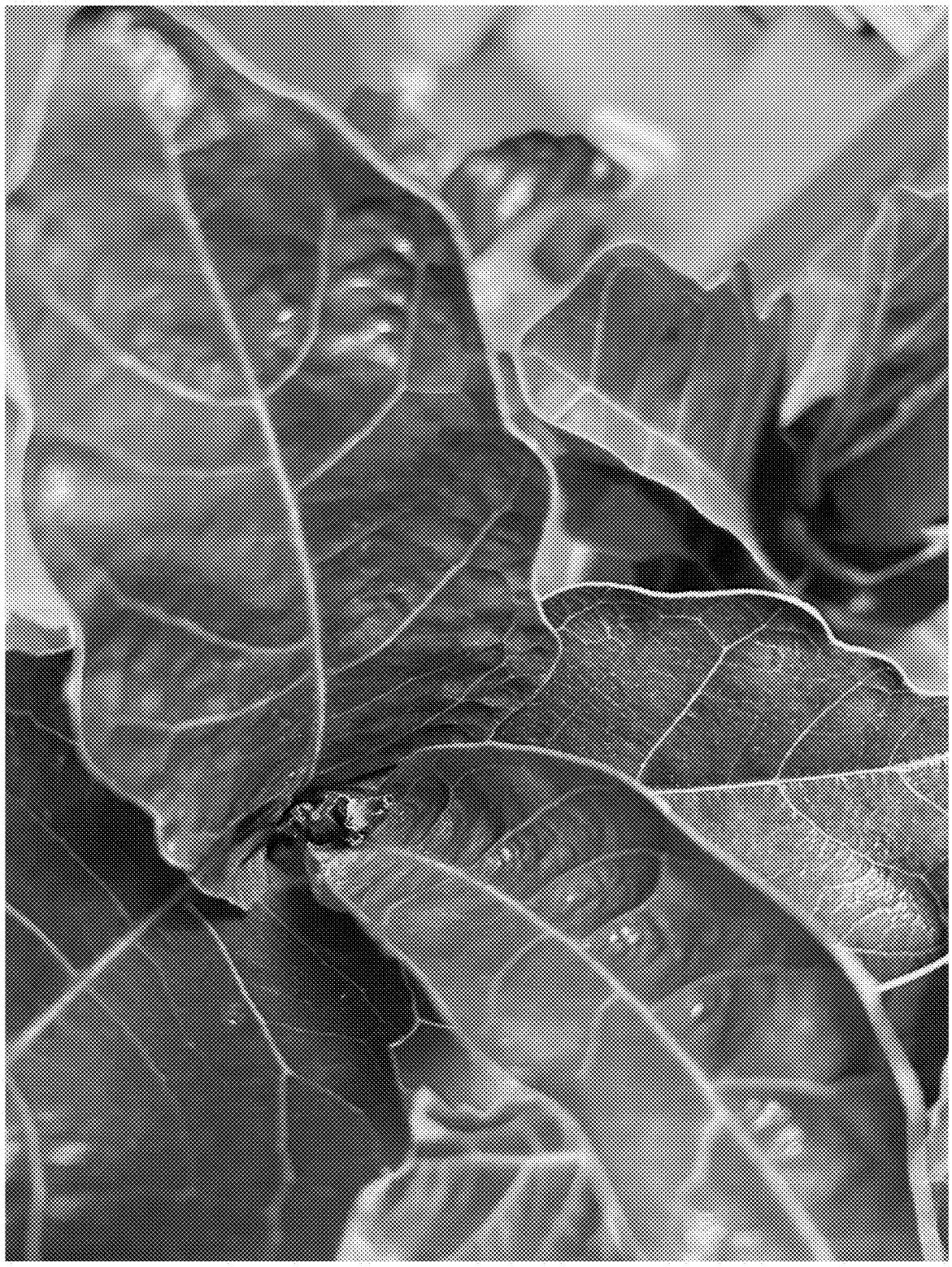

The photograph of FIG. 8 comprises a close-up view of typical leaves of the new *Ficus.*

Figure 9:
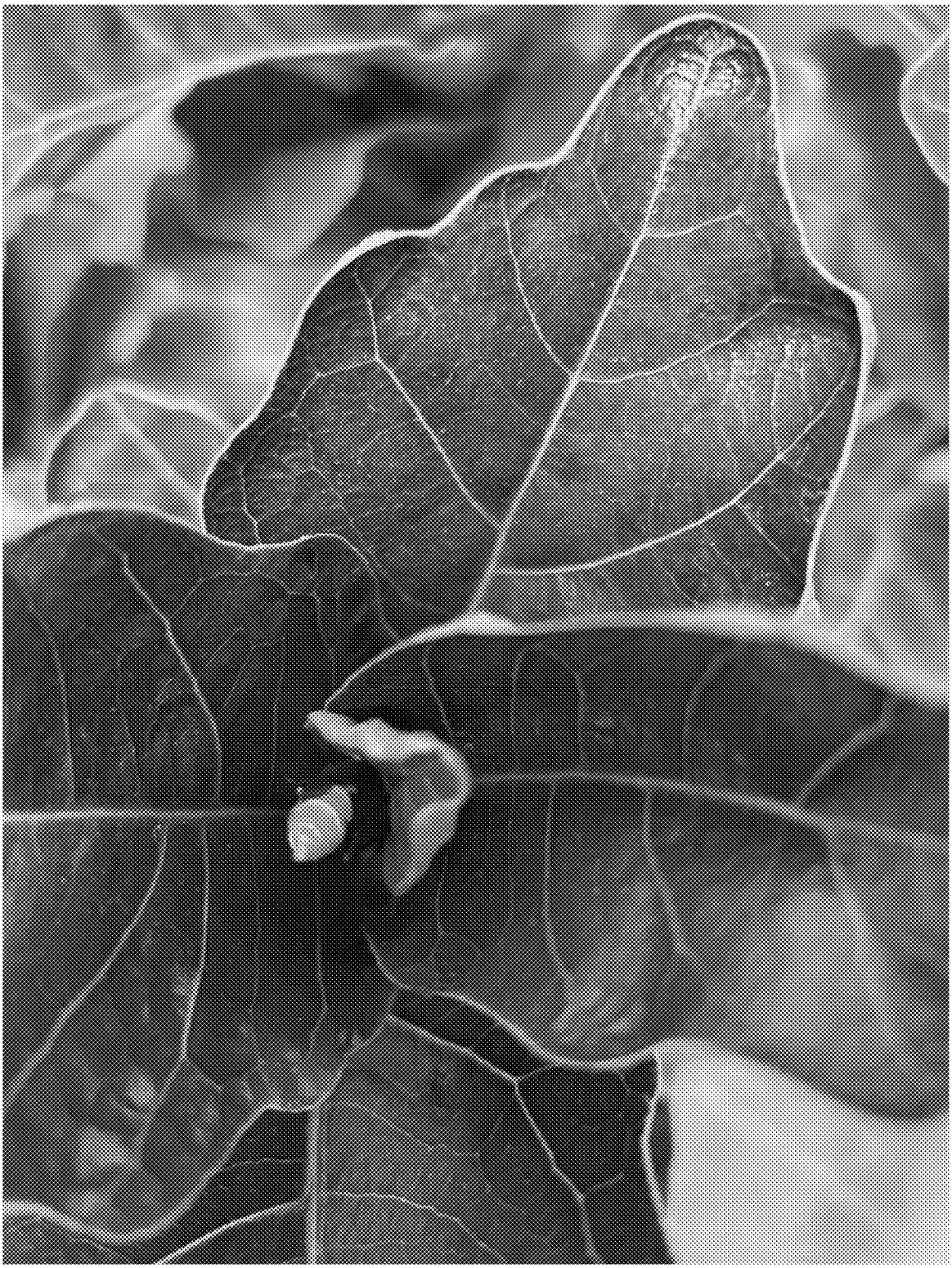

The photograph of FIG. 9 comprises a close-up view of typical leaves of the new *Ficus.*

Figure 10:
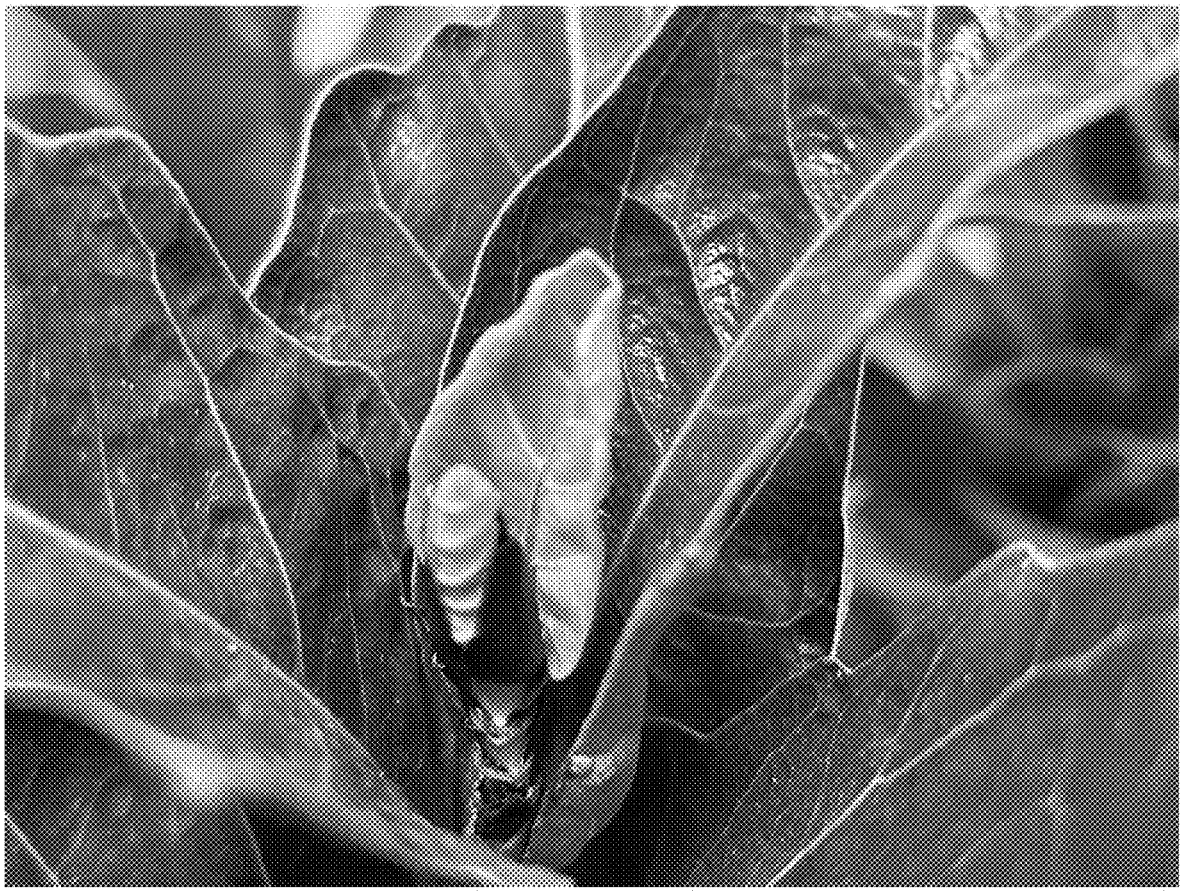

The photograph of FIG. 10 comprises a close-up view of typical leaves of the new *Ficus.*

Figure 11:
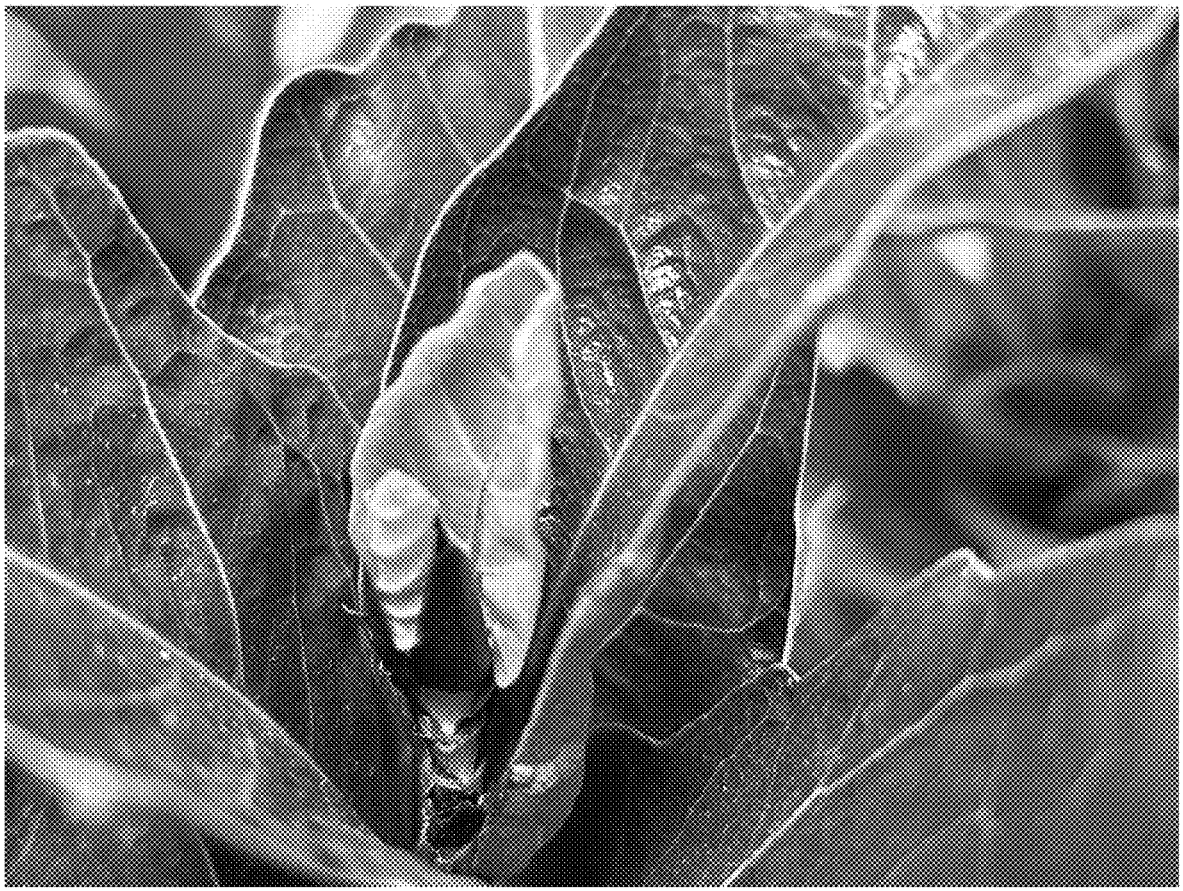

The photograph of FIG. 11 comprises a close-up view of typical leaves of the new *Ficus.*

Figure 12:
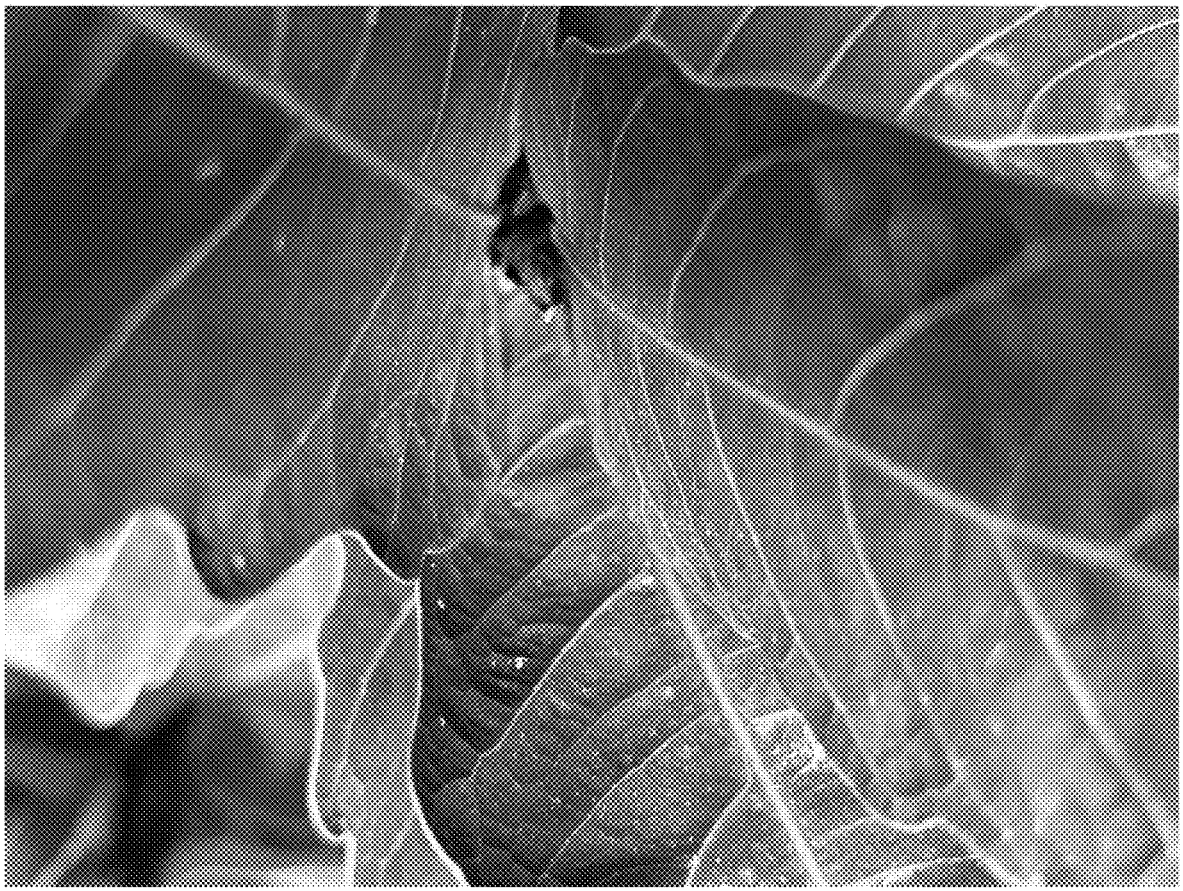

The photograph of FIG. 12 comprises a close-up view of typical leaves of the new *Ficus.*

Figure 13:
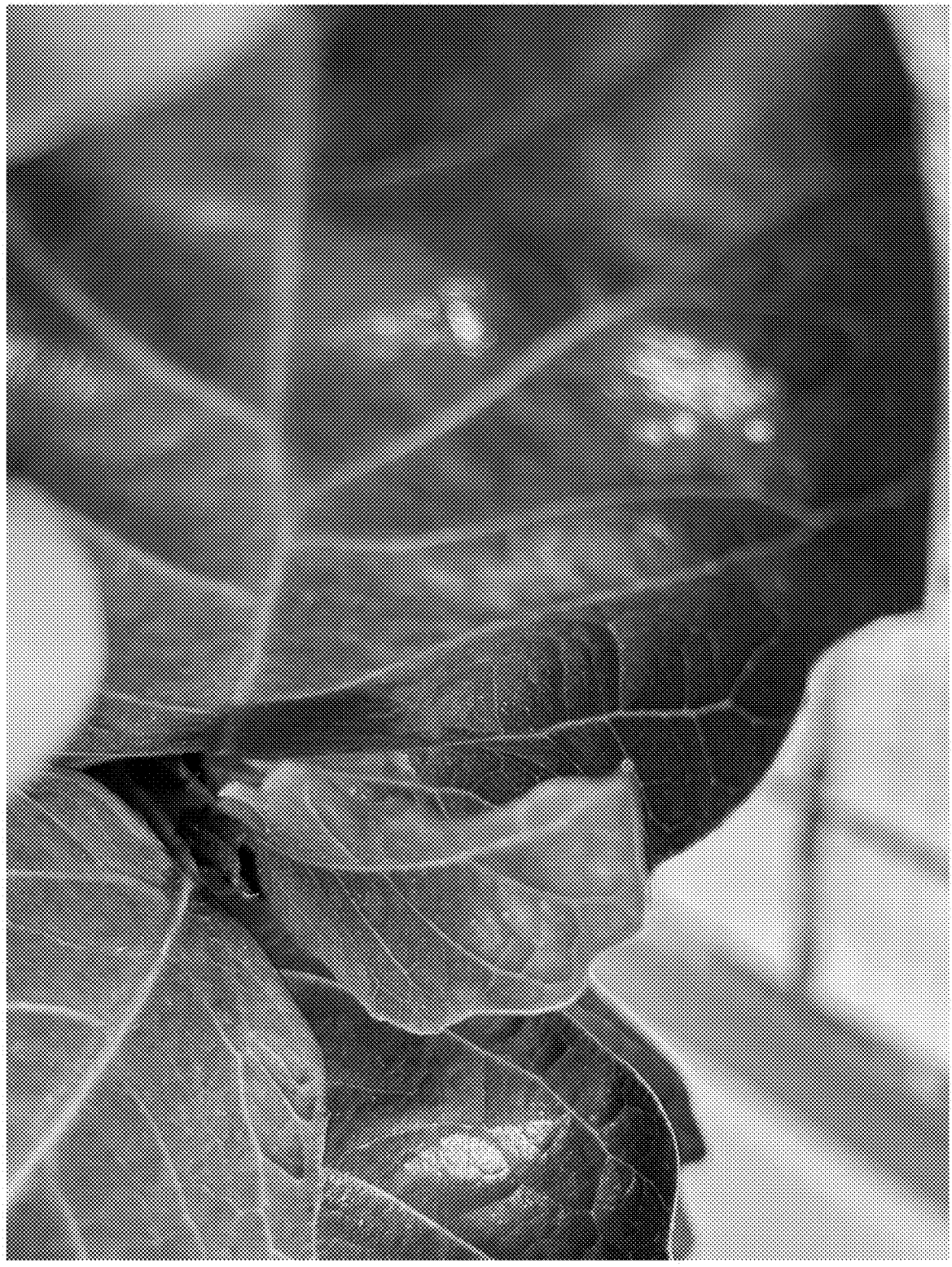

The photograph of FIG. 13 comprises a close-up view of typical leaves of the new *Ficus.*

DETAILED DESCRIPTION

The cultivar *Ficus* has not been observed under all possible environmental conditions. The phenotype may vary somewhat with variations in environment such as temperature and light intensity without, however, any variance in genotype.

The aforementioned photographs and following observations and measurements describe plants of the new *Ficus* that were grown in an outdoor nursery in Miami, Florida in partial shade to low light conditions in a 17 inch pot. During the production of the plants, day temperatures averaged about 82° F. Plants used for the photographs and description were about 2 years from planting. Color references are made to The Royal Horticultural Society Colour Chart, version 1995, except where general terms of ordinary dictionary significance are used.

PLANT

Botanical classification: *Ficus Lyrata.*

Propagation:

*Type*.—By cuttings.

*Time to initiate roots*.—About 21 days at 82° F.

*Time to produce a rooted plant*.—About 45 days at 82° F.

*Root description*.—Branching, 1A, 2C, 17A.

Plant description:

*Appearance*.—Upright growth with branching when pruned. Mounded and symmetrical.

*Growth rate/vigor*.—Fast growth with healthy and rapid development.

*Plant height*.—About 5 ft.

*Branching habit*.—Minimal branching habit.

*Main stems*.—Number: One. Length: About 18 inches. Diameter: About 1 inch. Internode length: About ¼ to ½ inch. Attitude: Straight Growth Habit. Aspect: Vertical. Strength: Strong as compared to other *Ficus* of similar size, no support needed for straight growth. Texture: Rough. Pubescence: Flakey. Color: 143B, 177C, 166A.

*Foliage*.—Length: About 6 inches. Width: About 2.5 to 3.5 inches. Shape: Oblong width, elongated with parallel sides. Shape of apex: Apiculate with serrations. Shape of base: Cordate with serrations. Orientation and aspect: Undivided. Texture: Upper surface: Smooth. Lower surface: Slightly rough and wavy; no pubescence. Margin type: Serrate. Young leaves: Upper surface color: 139A. Lower surface color: 143A. Fully expanded leaves: Upper surface color: 139A. Lower surface color: 143A. Venation: Pinnate and brochidodromous. Upper surface color: 152A, 146A, 144C. Lower surface color: 151A, 144A. Petiole: Length: About 1 centimeter. Diameter: About ¼ inch. Texture: Smooth. Color: 143A. Stipule: Shape: Conical cap-like. Shape of Apex: Aristate. Shape of Base: Cordate. Length: About 1½ to 2 inch. Diameter: About ¼ to ½ inch. Texture: Upper Surface: Coarse. Lower Surface: Coarse. Color: 175A.

Flower: Flower development has not been observed on plants of the new *Ficus* grown under commercial production conditions.

Disease/pest resistance:

*Disease resistance*.—Additional disease resistance has not been observed on plants of the new *Ficus* grown under commercial production conditions.

*Pest resistance*.—Additional pest resistance has not been observed on plants of the new *Ficus* grown under commercial production conditions.

Weather tolerance:

*Temperature tolerance*.—About 46° F.-96° F.

*Drought tolerance*.—Good, plant conserves water and exhibits reduced maintenance time.

It is claimed:

1. A new and distinct cultivar of *Ficus Lyrata*, named 'GM3X25002' as illustrated and described herein.

* * * * *